United States Patent
Kern et al.

(10) Patent No.: US 9,598,379 B2
(45) Date of Patent: Mar. 21, 2017

(54) PROCESS FOR PREPARING MELAMINE

(75) Inventors: Andreas Kern, Mannheim (DE); Hans-Ulrich Pröbstle, Bobenheim-Roxheim (DE); Tilo John, Speyer, DE (US); Wolfgang Steiner, Friedelsheim (DE); Heiko Maas, Lantau Island (CN)

(73) Assignee: BASF SE, Ludwigshafen (DE)

( * ) Notice: Subject to any disclaimer, the term of this patent is extended or adjusted under 35 U.S.C. 154(b) by 1074 days.

(21) Appl. No.: 12/738,049

(22) PCT Filed: Oct. 14, 2008

(86) PCT No.: PCT/EP2008/063804
§ 371 (c)(1),
(2), (4) Date: Apr. 14, 2010

(87) PCT Pub. No.: WO2009/050169
PCT Pub. Date: Apr. 23, 2009

(65) Prior Publication Data
US 2010/0222582 A1  Sep. 2, 2010

(30) Foreign Application Priority Data

Oct. 15, 2007  (EP) .................................... 07118498

(51) Int. Cl.
*C07D 251/60*  (2006.01)
*C07D 251/62*  (2006.01)

(52) U.S. Cl.
CPC ......... *C07D 251/60* (2013.01); *C07D 251/62* (2013.01)

(58) Field of Classification Search
CPC ............................ C07D 251/60; C07D 251/62
USPC .................................................. 544/203, 201
See application file for complete search history.

(56) References Cited

U.S. PATENT DOCUMENTS

| | | | | |
|---|---|---|---|---|
| 3,697,521 A | * | 10/1972 | Van Nassau et al. | 544/201 |
| 4,348,520 A | * | 9/1982 | Bruls et al. | 544/201 |
| 7,253,280 B2 | | 8/2007 | Kuhrs et al. | |

FOREIGN PATENT DOCUMENTS

| | | |
|---|---|---|
| DE | 2060929 A1 | 6/1971 |
| DE | 3302833 A1 | 8/1984 |
| EP | 0018695 A1 | 11/1980 |
| WO | WO-2004/065371 A1 | 8/2004 |

OTHER PUBLICATIONS

International Preliminary Report on Patentability for PCT/EP2008/063804, dated Apr. 20, 2010.
Ripperger, W., "The World Melamine Industry," Nitrogen, Nr. 228, Jul. 1, 1997, pp. 43-51, XP000693900.

* cited by examiner

*Primary Examiner* — Venkataraman Balasubramanian
(74) *Attorney, Agent, or Firm* — Drinker Biddle & Reath LLP

(57) ABSTRACT

Process for preparing melamine by converting urea in the presence of a solid catalyst in one reactor or in a plurality of reactors connected in series in the temperature range from 370° C. to 430° C., cooling and filtering the gas formed in the urea conversion, removing the melamine by desublimation and recycling a portion of the gas present after the melamine removal ("cycle gas") into the reactor or the reactors, which comprises performing all of the above stages at a pressure in the range from 4 bar abs. to 10 bar abs.

9 Claims, No Drawings

PROCESS FOR PREPARING MELAMINE

CROSS REFERENCE TO RELATED APPLICATIONS

This application is a national stage application under 35 U.S.C. §371 of PCT/EP2008/063804, filed Oct. 14, 2008, which claims benefit to European application 07118498.0, filed Oct. 15, 2007, the entire disclosures of which are hereby incorporated by reference.

The invention relates to an improved process for preparing melamine (2,4,6-triamino-1,3,5-triazine) by thermal conversion of urea in the presence of a catalyst.

Melamine finds use for preparing melamine resins by reaction with carbonyl-containing compounds. Among other uses, the resins are used as plastics and in paints and coatings.

The preparation of melamine by decomposition of urea is a known reaction which is utilized in several variants by the chemical industry. An overview can be found in Ullmann's Encyclopedia of Industrial Chemistry, 5th Edition 1990, vol. A 16, pages 171 to 185.

In principle, a distinction is drawn between the high-pressure process and the low-pressure process. The pressure data hereinafter are in bar (abs.).

The high-pressure process is typically performed at pressures of more than approx. 80 bar (abs.) and temperatures of more than 370° C., the melamine being synthesized in a noncatalytic manner in a melt.

The low-pressure process is generally performed at pressures of from approx. 1 bar (abs.) to approx. 10 bar (abs.) and temperatures of from 370 to 430° C. in a heterogeneous catalysis.

According to the state of knowledge to date, the reaction in the catalytic low-pressure process proceeds in two steps. In the first, endothermic step, urea decomposes to give ammonia and isocyanic acid, which trimerizes in the second, exothermic step to give melamine with release of carbon dioxide. The overall reaction (first plus second step) is endothermic.

There exist essentially three variants of the low-pressure process, which will be addressed briefly hereinafter. Further details can be taken from Ullmann's Encyclopedia of Industrial Chemistry, 5th Edition 1990, vol. A 16, pages 171 to 185.

In the Linz-Chemie process, the reaction is carried out in two stages. In the first stage, urea melt is decomposed at 350° C. and 3.5 bar (abs.) in a sand fluidized bed to give ammonia and isocyanic acid. Subsequently, in a fixed bed reactor, isocyanic acid is converted at 450° C. and atmospheric pressure catalytically to melamine. The catalyst is generally an aluminum oxide catalyst. The reaction gas comprising gaseous melamine is cooled ("quenched") with water and the melamine is thus removed from the reactor gas. The aqueous melamine suspension is worked up further, in a relatively complicated manner, in solid/liquid separation stages.

The DSM-Stamicarbon process is a one-stage process which is carried out at approx. 7 bar (abs.). The catalysts used are aluminum silicates or zeolite-containing catalysts, which are used in a fluidized bed. The fluidizing gas used is pure ammonia, which is recovered from the workup stage. The reaction gas comprising gaseous melamine is cooled with water, and the melamine is thus removed from the reactor gas. The aqueous melamine suspension is worked up further, in a relatively complicated manner, in solid/liquid separation stages.

In the previous BASF process, finally, a fluidized bed is likewise employed at low pressure (approx. 2 bar (abs.)), using aluminum oxide or aluminum oxide-silicon dioxide catalysts, and ammonia and carbon dioxide functions as the fluidizing gas (also known as process gas). The hot, gaseous melamine, in contrast to the Linz-Chemie and DSM-Stamicarbon process, is desublimed in a crystallizing apparatus (also known as "crystallizer") by cooling to approx. 200° C., and a fine crystalline powder is obtained, which is then transported into a cyclone in a gas stream and is separated there from the gas. The gas which, as well as ammonia and carbon dioxide, may comprise further impurities, is then fed to a so-called urea scrubber, in which it is then freed of the impurities at approx. 135° C. and cooled. A portion of the gas is then fed to the reactor as gas for the fluidized bed ("fluidizing gas") and thus reenters the circulation system. Another portion of the gas is fed into the crystallizer for cooling, and a last portion of the gas leaves the circulation system as offgas.

Even though the existing processes are used on the industrial scale, there is still room for improvements.

The high-pressure processes for melamine synthesis have comparatively low single-line capacities of approx. 30000 t/year.

The single-line capacity is the maximum amount of melamine which can be obtained from a reaction and workup unit per year.

The BASF low-pressure process, for example, also has a relatively low single-line capacity of approx. 40000 t/year.

The DSM process at somewhat higher pressures does have a greater single-line capacity of approx. 80000 t/year. However, the disadvantage of this process is the complicated removal, particularly in terms of apparatus and energy, of the melamine by quenching with water (wet workup).

Still not all processes in the melamine synthesis according to the prior art processes are understood. There is much room for speculation, for example, if the intention is to explain the site, nature and reaction conditions for the formation of by-products and conversion products of melamine. Conversion products of melamine may, according to the reaction conditions, for example, be the melem, melons and melam which are specified in Ullmann's Encyclopedia of Industrial Chemistry, 5th Edition 1990, vol. A 16, pages 171 to 185 and are thought to form through the reaction of melamine molecules.

Further by-products or conversion products are ammelin, ammelide or cyanuric acid (formal replacement of one, two or three —$NH_2$ groups of melamine by —OH), which are likewise specified in Ullmann's Encyclopedia of Industrial Chemistry, 5th Edition 1990, vol. A 16, pages 171 to 185. It is not clear whether these products are built up from smaller molecules, under the conditions which exist in the melamine process, and/or are formed through (partial) hydrolysis of already formed melamine.

It is thus a great challenge to remove the small amount of by-products and conversion products of melamine from the desired main product, melamine, or not to allow the by-products and conversion products to form in a significant amount at all, all with a high annual capacity of the industrial scale melamine synthesis.

There is the risk that yields and further characteristics (for example morphology, purity) of the melamine change when one or more essential parameters (for example pressure and temperature) change in the melamine process, in the course of synthesis and/or in the course of workup.

It is an object of the invention to provide an economically more attractive process for preparing melamine from urea without any deterioration in the product properties, for example morphology and purity, of the melamine.

The object is achieved by the process as defined in the claims.

The process according to the invention will be described in detail hereinafter. The main features of the process according to the invention are analogous to the BASF process described in Ullmann's Encyclopedia of Industrial Chemistry, 5th Edition 1990, vol. A 16, pages 171 to 185.

The process gas of the melamine synthesis, consisting of ammonia and $CO_2$ in a mass ratio of approx. 1:1, is formed in the melamine synthesis from urea. The gas is generally compressed by from approx. 0.5 to 2 bar and then heated to from 370° C. to 430° C., before it is fed into the fluidized bed reactor as the fluidizing gas. This gas stream comes out of the urea scrubber and, in a preferred embodiment of the invention, directly from the gas circulation system after the melamine separation, as described in detail below.

The urea to melamine reaction can be carried out in one reactor or in a plurality of reactors connected in series. The reaction is preferably carried out in one reactor or in two reactors connected in series. When the reaction is carried out in two reactors connected in series, the catalyst may be present in the form of a fluidized bed both in the first and in the second reactor, but the catalyst is preferably present in the form of a fixed bed in the second reactor. In the case of two reactors connected in series, reference is also made to a main reactor and secondary reactor.

Preference is given to performing the melamine preparation in one reactor.

Particular preference is given to performing the melamine preparation in one reactor in a fluidized bed.

The hot fluidizing gas consisting of ammonia and carbon dioxide in a mass ratio of approx. 1:1 is fed to the reactor filled with catalyst and fluidizes the solid.

The catalyst used in the fluidized bed reactor is a customary catalyst for catalytic melamine synthesis based on inorganic Lewis acids, preferably Lewis-acidic metal oxides, such as aluminum oxides or silicon aluminum oxides.

A urea melt is sprayed into the reactor together with ammonia as the atomizing gas. The reactor temperature is in the range from 370° C. to 430° C., preferably in the range from 390° C. to 420° C.; the reactor pressure is in the range from 4 bar (abs.) to 10 bar (abs.), preferably in the range from 5 bar (abs.) to 8 bar (abs.).

The reaction gas leaves the reactor via an installed cyclone separator, which removes entrained fine fractions of catalyst and returns them to the fluidized bed. At the reactor outlet, the process gas consists of melamine, by-products, unconverted isocyanic acid, and ammonia and carbon dioxide.

The conversion of urea to melamine is in the range from 70% by weight to 97% by weight, based on urea; the conversion of urea to melamine is preferably in the range from 80% by weight to 97% by weight, based on urea; the conversion of urea to melamine is especially in the range from 90% by weight to 97% by weight, based on urea.

The reaction gas from the melamine reactor or if appropriate postreactor, which is at from 370° C. to 430° C., flows through a gas cooler which cools the melamine-containing reaction gas to a temperature in the range from 320° C. to 380° C., preferably in the range from 330° C. to 370° C. At these temperatures, high-boiling by-products begin to desublime and/or precipitate on the catalyst dust not retained by the cyclones in the fluidized bed reactor. The melamine, which is still in gaseous form, is thus substantially purified to free it of the relatively high-boiling secondary components. According to the present state of knowledge, the temperature in the gas cooler determines the melem content in the melamine and the melamine content in the by-product-containing catalyst dust. The total amount of secondary components still in gaseous form (based on melamine) in the reaction gas is surprisingly not higher than in the process customary to date.

The reaction gas is then fed into hot gas filters. There, the catalyst dust not retained by the cyclones in the fluidized bed reactor and the by-products desublimed in the gas cooler are separated out. The gas leaving the hot gas filter typically has a temperature in the range from 320° C. to 380° C. and generally comprises, apart from melamine, only traces of the high-boiling by-products such as melam, melem and also unconverted isocyanic acid. The catalyst dust is discharged from the filter, typically via a pressure lock, and disposed of.

Gas coolers and hot gas filters may be duplicated and be operated in an A-B sequence.

The reaction gas coming from the hot gas filter is mixed in the crystallizer, at a pressure in the range from 4 bar (abs.) to 7 bar (abs.), preferably in the range from 5 bar (abs.) to 6 bar (abs.), with the gas which has been scrubbed in the urea scrubber and cooled to a temperature in the range from 130° C. to 150° C., preferably from 135° C. to 150° C. (so-called "cooling gas", composition like the fluidizing gas), and thus cooled to a temperature in the range from 150° C. to 250° C., preferably in the range from 200° C. to 250° C., more preferably in the range from 210° C. to 230° C. This typically desublimes melamine almost completely, and it is generally obtained as a fine white powder.

For example, the crystal morphology of melamine, measured by the method of scanning electronmicroscopy (SEM), is like that of current commercial products. SEM analysis is known per se. To determine the crystal morphology of melamine, the procedure may be as follows. The melamine powder is scattered on to a conductive adhesive carbon pad and, to increase the conductivity, sputtered with 2.5 nm of platinum, and then the surface is imaged in the SEM. The acceleration voltage is 3 kV; the images are made with the secondary electron detector at an angle of inclination of 13 degrees.

The particle size distribution also corresponds to the customary standard. The particle size distribution of the melamine can be determined by laser diffraction (method according to ISO 13320). To this end, the melamine powder is dry-dispersed with a dispersion pressure of 2 bar and, for example, analyzed in a Mastersizer S analytical instrument (from Malvern) with the following analysis parameters: gas velocity 157 m/s; scatter model 3$$A (Fraunhofer); focal length 300 mm; beam path 10.00 mm.

For example, the d-50 value (mean particle diameter) of the melamine powder obtainable by the process according to the invention is in the range from 10 μm to 30 μm, and the d-90 value is in the range from 30 μm to 50 μm.

The desublimed melamine is generally conveyed pneumatically into cyclones, separated out there, discharged and conveyed further to the filling stage.

The reaction gas leaving the melamine cyclone ("cycle gas") has a temperature in the range from 200° C. to 250° C., preferably from 210° C. to 230° C., and comprises, apart from ammonia and carbon dioxide, also residues of melamine dust, isocyanic acid and other by-products. The amount of isocyanic acid is in the range from 0.1% by volume to 2.0% by volume, preferably from 0.1% by volume to 1.0% by volume.

In a preferred embodiment, a portion of this hot cycle gas—preferably an amount of gas in the range from 5% to 50%, more preferably in the range from 10% to 20%, based in each case on the total amount of gas from the cyclone—after the melamine separation, without passing through the urea scrubber, is fed back into the melamine synthesis reactor as fluidizing gas ("warm fluidizing gas").

This warm fluidizing gas can be branched off at any point in the cycle gas path downstream of the melamine separation and upstream of the cycle gas scrubbing stage in the urea scrubber. For instance, the warm fluidizing gas can be branched off directly downstream of the cooling gas blower, which typically conveys the cycle gas to the urea scrubber, in flow direction, and be conveyed into the melamine synthesis reactor. However, preference is given to branching off the warm fluidizing gas upstream of the cooling gas blower, which typically conveys the cycle gas to the urea scrubber, in flow direction, and conveying it into the melamine synthesis reactor.

The cycle gas residue, i.e. the amount of cycle gas after the melamine separation which has not been branched off in accordance with the invention, is typically conveyed to the urea scrubber by means of a cooling gas blower. There, the cycle gas residue is finally cooled in a scrubber operated with urea circulation to a temperature in the range from 130° C. to 150° C., preferably from 135° C. to 140° C.

In this apparatus, the remaining isocyanic acid typically recombines with ammonia to give urea, which is fed back into the melamine synthesis reactor.

The cooled cycle gas residue leaving the urea scrubber is then, after customary purification, for example removal of urea droplets in urea separation cyclones, recycled partly as cooling gas into the crystallizing apparatus and removed partly as offgas of the overall process.

The process according to the invention is notable for advantages including the following:

Operation in the relatively high pressure range in accordance with the invention allows a significant reduction in the specific apparatus volumes and hence actually enables the construction of a single-line plant for capacities of typically at least 60000 t/a. As a result of the raising of the pressure level, there is a fall in the operating volume flows and hence in the specific energy consumption (energy consumption per ton of melamine) of fluidizing gas compressor and cooling gas compressor with the pressure drops in the system kept constant.

By virtue of a preferred embodiment of the invention, specifically by virtue of the above-described modified cycle gas path, compared to the prior art, the amount of cycle gas which has to date been conducted through the cooling gas blower, the urea scrubber and the urea separation cyclones is reduced by a substantial amount.

The urea circulation via the urea scrubber is reduced to an equal degree, such that, as well as the apparatus mentioned, the urea pump(s) and urea heat exchanger can also become smaller.

In addition, the heating output of the fluidizing gas heater is reduced, since the gas inlet temperature is increased from the range from 140° C. to 200° C. to the range from 210° C. to 250° C.

The reduction in the capital costs and the savings in power consumption (cooling gas blower and urea pump(s)) and in the natural gas consumption of the salt heater are the advantages of the modified gas pathway.

The melamine obtainable by the process according to the invention is notable for high purity and can be processed further directly.

The purity of melamine achieved by the process according to the invention, determined by the method of turbidity measurement based on (DIN) EN ISO 7027, is less than 15 NTU (nephelometric turbidity units). The turbidity measurement of a melamine sample can be carried out, for example, in a HACH turbidimeter as follows. 14 g of melamine, 20.4 ml of 30% formalin and 2 ml of distilled water are initially charged. The sample is heated electrically (hotplate or heating mantle) and allowed to boil for exactly 30 seconds. The sample is then cooled in a thermostat set to 35° C. within exactly 3 minutes with occasional stirring to approx. 50° C., filled into a round cuvette and analyzed in the turbidimeter.

The invention claimed is:

1. A process for preparing melamine by converting urea in the presence of a solid catalyst in one reactor or in a plurality of reactors connected in series in the temperature range from 370° C. to 430° C., cooling the gas formed in the urea conversion in a gas cooler to a temperature from 320° C. to 380° C. and filtering the gas formed in the urea conversion in a hot gas filter, removing the melamine by desublimation and recycling a portion of the gas present after the melamine removal ("cycle gas") into the reactor or the reactors, which comprises performing all of the above stages at a pressure in the range from 4 bar abs. to 10 bar abs and wherein, after the melamine removal, 5 to 50% of the cycle gas is branched off and fed into the reactor as "fluidizing gas" without passing through a urea scrubber and at least some of the remainder of cycle gas is fed to the urea scrubber.

2. The process according to claim 1, wherein the catalytic urea conversion and melamine synthesis take place only in one reactor in a fluidized bed.

3. The process according to claim 1, wherein the return gas is branched off upstream of the cooling gas blower in flow direction.

4. The process according to claim 1, wherein the desublimation is carried out at a temperature in the range from 150° C. to 250° C.

5. The process according to claim 2, wherein the desublimation is carried out at a temperature in the range from 150° C. to 250° C.

6. The process according to claim 3, wherein the desublimation is carried out at a temperature in the range from 150° C. to 250° C.

7. The process according to claim 2, wherein the return gas is branched off upstream of the cooling gas blower in flow direction.

8. The process according to claim 7, wherein the desublimation is carried out at a temperature in the range from 150° C. to 250° C.

9. The process according to claim 1, wherein 10 to 20% of the cycle gas is branched off and fed into the reactor as "fluidizing gas" without passing through the urea scrubber.

* * * * *